United States Patent [19]

Koestler

[11] 4,360,376

[45] Nov. 23, 1982

[54] MICROENCAPSULATED TRIFLURALIN

[75] Inventor: Robert C. Koestler, Wayne, Pa.

[73] Assignee: Pennwalt Corporation, Philadelphia, Pa.

[21] Appl. No.: 251,606

[22] Filed: Apr. 6, 1981

Related U.S. Application Data

[63] Continuation-in-part of Ser. No. 221,174, Jan. 29, 1981, abandoned, which is a continuation of Ser. No. 12,095, Feb. 14, 1979, abandoned, which is a continuation-in-part of Ser. No. 887,576, Mar. 17, 1978, abandoned.

[51] Int. Cl.$^3$ .......................................... A01N 25/28
[52] U.S. Cl. ................................ 71/121; 71/DIG. 1; 424/32
[58] Field of Search .............. 71/DIG. 1, 121; 424/32

[56] References Cited

U.S. PATENT DOCUMENTS

| 3,074,845 | 1/1963 | Geary | 424/32 |
|---|---|---|---|
| 3,257,190 | 6/1966 | Soper | 71/94 |
| 3,403,180 | 9/1968 | Soper | 71/121 |
| 3,516,941 | 6/1970 | Matson | 71/DIG. 1 X |
| 3,523,906 | 8/1970 | Vrancken et al. | 71/DIG. 1 X |
| 3,539,465 | 11/1970 | Hiestand et al. | 71/DIG. 1 |
| 3,577,515 | 5/1971 | Vandegaer | 424/32 |
| 3,607,776 | 9/1971 | Santo et al. | 424/32 |
| 3,748,277 | 7/1973 | Wagner | 71/DIG. 1 X |
| 3,959,464 | 5/1976 | De Savigny | 424/78 |
| 4,056,610 | 11/1977 | Barber, Jr. et al. | 424/32 |

*Primary Examiner*—Catherine L. Mills

[57] ABSTRACT

Aqueous dispersions of microcapsules of an organic solvent solution of trifluoro-2,6-dinitro-N,N-dialkyl-p-toluidine wherein said microcapsules are formed with a polycondensate wall are disclosed herein to provide improved herbicidal compositions especially for large scale application to crop producing areas.

10 Claims, No Drawings

MICROENCAPSULATED TRIFLURALIN

BACKGROUND

Cross-references

This application is a continuation-in-part of copending application Ser. No. 221,174 filed Jan. 29, 1981, now abandoned, which is a continuation of application Ser. No. 012,095 filed Feb. 14, 1979, now abandoned, which in turn is a continuation-in-part of application Ser. No. 887,576 filed Mar. 17, 1978, now abandoned.

PRIOR ART DISCUSSION

Trifluralin is the generic name for alpha, alpha, alpha-trifluoro-2,6-dinitro-N,N-dipropyl-p-toluidine, a product of the Elanco Division of Eli Lilly and Company sold in a pre-emergent herbicide composition under the trademark "Treflan". As a selective preemergent type herbicide, it has applications on many crops including cotton, soybeans, safflower, sunflower, beans, peas, sugar beets, castor beans, rapeseed, established ornamentals; transplants of cabbage, cauliflower, broccoli, brussels sprouts, tomatoes and pepper; non bearing vineyards; citrus trees; established alfalfa, carrots and potatoes. Its use to eliminate germinating and seedling weed grasses is covered by U.S. Pat. No. 3,257,190.

Trifluralin, as a pre-emergent herbicide, is available as an emulsifiable concentrate (E.C.) or in granules. To obtain optimum effectiveness, both forms must be worked into the soil surface after application. The granular product is applied by conventional tractor driven equipment and is simultaneously incorporated into the top 2-3 inches of the soil. The E.C., on the other hand, is preferably applied at a rate of about 0.75-1.25 pounds of active ingredient per acre by aerial spraying since vast acreage can be sprayed quickly and economically by this mean. Applications of the E.C., however, must be incorporated within four (4) hours after spraying (as stated on the product label) in order to prevent loss of effectiveness of the treatment. It has been shown that vapor losses for unincorporated trifluralin, only three (3) hours after spraying, can be as much as 30%[1]. Thus, the great advantage of aerial spraying, rapid coverage of vast acreage, is lost due to the inability of the farmer to incorporate the treatment before it is dissipated by vaporization. A sprayable formulation of trifluralin that will not lose its active ingredient so rapidly by vaporization would allow the speed and economy of aerial application and a sufficient period for incorporation of the pesticide into the soil by the farmer without substantial loss in pesticidal activity prior to incorporation.

[1]. Parochetti, J. V. and Hein, E. R. Weed Science, Volume 21, Issue 5 (September 1973).

It is alleged in U.K. Specification No. 1,371,179 that premature volatilization or other deterioration of an active material may be avoided when the material is encapsulated. The persistency of certain pesticide products is increased when the product is encapsulated as shown, for example, in U.S. Pat. Nos. 3,577,515; 3,959,464; and W. A. Gentner et al., Publication of U.S.D.A. "The interference of Microencapsulation on The Herbicidal Performance of Chlorpropham", September, 1976. However, improvement in the effectiveness of any given pesticide may or may not be possible by encapsulating the pesticide in accordance with one of the several known encapsulation techniques. If it is found that encapsulation of a given pesticide is possible, achievement of useful results generally requires long experimentation with the encapsulation process and ingredients to provide a potentially effective product. The full development of a product entails extensive greenhouse and field testing to establish usefulness for various crop applications. Reformulation of the encapsulation recipe after testing, followed by further testing, is not an unusual requirement.

STATEMENT OF THE INVENTION

This invention is a herbicide product comprising an aqueous dispersion of microcapsules of a solution of alpha, alpha, alpha-trifluoro-2,6-dinitro-N,N-di($C_1$–$C_5$) alkyl-p-toluidine dissolved in at least 20% up to about 60%, based on the weight of said solution, of a water insoluble, organic solvent therefor, said solution microencapsulated within a resinous polycondensate wall selected from the group consisting of polyurea, polyamide and amide-urea copolymers, the weight of said walls ranging from about 2.5 to about 40%, based on the weight of said microcapsules, said microcapsules having an average size ranging from about 10 to about 100 microns, said polycondensate wall prepared by the reaction of first and second polyurea, polyamide, or amide-urea copolymer-forming intermediates, at least one of said first and second intermediates containing from 0 to 100 percent, based on the weight of the intermediate, of a polyfunctional reactant which is (a) complementary to the other of said intermediates and effective for crosslinking reaction and (b) has at least three reactive groups that are effectively functional in said reaction, said reactive groups, selected from the class consisting of amine, isocyanate, —COCl and $SO_2Cl$ groups, and said intermediate containing at least 5% of said polyfunctional reactant when the weight of said wall is 10% or less, but said polyfunctional reactant being less than 100% of said intermediate when the weight of said wall is 10% or greater.

EXAMPLE

This invention is demonstrated using trifluralin as the active herbicide material because of its availability and extensive use in the field. However, similar results are anticipated with microencapsulated herbicides closely related to trifluralin wherein the alkyl groups attached to the nitrogen contain 1,2,4 or 5 carbon atoms.

Microencapsulated trifluralin samples having capsule walls of amide-urea copolymer of varying formulations, polyurea and polyamide are prepared in accordance with the interfacial polycondensation procedure described hereinafter. These samples, identified by an alpha-numeric system explained below, are investigated in greenhouse test procedures to determine the comparative herbicidal activity of such samples and the emulsifiable concentrate (E.C.) of trifluralin[2] when (a) applied to the soil surface and (b) incorporated into the soil seven (7) days after application to the soil.

[2]. Emulsifiable concentrate contains the active herbicide, an organic solvent therefor and a surfactant. It is diluted with water for application to the soil.

The alpha-numeric system used to identify the microencapsulated samples is exemplified by the set 15/5/SP30. In this set, the numeral 15 represents a wall weight of 15%, based on the weight of the microcapsule (wall+capsule content); the numeral 5 refers to the replacement of 5% of the difunctional acid-derived reactant in the capsule forming recipe with a polyfunctional crosslinking agent (polymethylene polyphenyl-isocyanate); the letter S indicates the use of sebacoyl chloride as the acid-derived difunctional reactant; the letter P refers to the use of Panasol AN-2 (aromatic petroleum solvent) as the solvent; and the numeral 30 in the set shows that 30% of the solvent, based on the weight of the encapsulated trifluralin solution, is used as the solvent in the trifluralin solution. A change in one or more of the set numbers indicates a change in the percentage of wall weight, crosslinking agent or solvent used. The letter P in the set may be replaced with either T, X, or t. T represents toluene, X represents xylene and t represents Tennaco solvent (aromatic petroleum solvent).

Test Procedures

Metal flats having a depth of three inches and filled with nonsterilized medium textured greenhouse soil are used in the tests.

To compare the herbicidal activity of microencapsulated trifluralin samples and an E.C. formulation of trifluralin against both food plants and weeds when applied to the soil surface, the soil in one metal flat for each of several plant species is sprayed with one of the encapsulated trifluralin formulations at a rate of 0.75 pound of trifluralin per acre. This procedure is repeated for each of the encapsulated trifluralin samples and the E.C. formulation. After spraying, the flats are immediately watered with one pint of water-soluble fertilizer preparation and then each flat planted with a single plant species including corn, soybean, cotton, foxtail millet, pigweed, crabgrass and velvet leaf. After 14 days, a plant injury observation is made, and the data reported in Table 1.

To compare the herbicidal activity of the microencapsulated trifluralin samples and E.C. formulation when the herbicide is incorporated into the soil seven days after application to the soil surface, metal flats filled with soil as described above, are used. The soil in the flats is subirrigated with an excess amount of water, and each of the E.C. and encapsulated herbicide samples, formulated in water, is sprayed on the soil surface of three different flats at a rate of 0.75 pounds of trifluralin per acre. In one E.C. treatment, the E.C. formulation is immediately incorporated into the soil, i.e., the soil for three flats is placed in a rotary mixer and the E.C. formulation is sprayed onto the soil as it tumbles; after incorporation is complete, the treated soil is then placed back in the flats and subirrigated.

After treatment, the flats are moved into a growth room which is maintained to simulate crop growing conditions and has a large air exchange capacity to enhance the volatility of the applied formulations. The flats are allowed to remain in the growth room for several days during which no additional water is added to the soil. After seven days, except for those three flats for which the E.C. formulation has been immediately incorporated, the formulations are incorporated into the soil of each flat by mixing in a rotary mixer. Thereafter each flat plus an untreated control is planted with twenty-five (25) grain sorghum seeds and twenty (20) cultivated oat seeds,[3] the soil is moistened with an aqueous solution of soluble fertilizer and the flats are moved into a greenhouse. Fourteen days after planting, the fresh weight is harvested and recorded. The percent inhibition of grain sorghum and oats growth is reported in Table 1. The control plantings, for which no herbicide is incorporated, are used in these tests to provide a basis for zero (0) percent inhibition of plant growth. Dash lines in the table represent those instances wherein test results were not recorded.

3. Grain sorghum and oats are used in the delayed incorporation test as convenient test species sensitive to the herbicide.

TABLE 1

| Group | Sample | Wall Formulation | Plant Injury Rating* | | | | | | | Delayed Incorporation Percent Inhibition | |
|---|---|---|---|---|---|---|---|---|---|---|---|
| | | | Cotton | Corn | Soybean | Foxtail Millet | Pigweed | Crabgrass | Velvet Leaf | Grain Sorghum | Oats |
| | 1 | 5/0/ST50 | — | 0 | 0 | 9.5 | 9 | 10 | 1 | 45 | 41 |
| | 2 | 5/0/ST50 | — | 8 | — | 10 | 9 | 10 | 2 | 31 | 34 |
| | 3 | 5/10/ST50 | — | 0 | 0 | 9 | 8 | 9.5 | 1 | 87 | 84 |
| I | 4 | 15/0/ST50 | — | 1 | 0 | 9.5 | 9 | 10 | 4 | 85 | 85 |
| | 5 | 15/0/ST50 | — | 0 | 0 | 9.5 | 9.5 | 10 | 2 | 88 | 85 |
| | 6 | 15/5/SX30 | 0 | 0 | — | 3 | 10 | 5 | 8 | 78 | 79 |
| | 7 | 5/10/ST50 | — | 0 | 0 | 0 | 2 | 8 | 2 | 100 | 92 |
| | 8 | 10/5/SP30 | 0 | 0 | — | 2 | 0 | 8 | 0 | 98 | 98 |
| | 9 | 10/50/S(HMDA)**P30 | 0 | 0 | — | 5 | 1 | 8 | 3 | 79 | 86 |
| | 10 | 10/100/X30 | 0 | 0 | — | 0 | 0 | 0 | 0 | 97 | 98 |
| | 11 | 12.5/5/SP30 | 0 | 1 | 0 | 4 | 2 | 7 | 2 | 85 | 94 |
| | 12 | 15/0/SP30 | 2 | 3 | 4 | 6 | 4 | 10 | 5 | 83 | 94 |
| II | 13 | 15/5/SP40 | 2 | 1 | 0 | 4 | 0 | 9 | 3 | 74 | 92 |
| | 14 | 15/5/SP30 | 4 | 2 | 2 | 5 | 0 | 8 | 3 | 87 | 93 |
| | 15 | 15/5/SP30 | 0 | 0 | — | 0 | 5 | 6 | 0 | 76 | 91 |
| | 16 | 15/10/ST50 | 0 | 1 | 1 | 0 | 5 | 7 | 3 | 61 | 65 |
| | 17 | 15/10/ST50 | — | 0 | 0 | 0 | 0 | 5 | 1 | 87 | 79 |
| | 18 | 15/10/ST50 | 0 | 0 | — | 1 | 0 | 4 | 1 | 82 | 91 |
| | 19 | 15/10/St10 | 0 | 0 | — | 0 | 0 | 0 | 0 | 67 | 93 |
| | 20 | 5/10/ST50 | 0 | 3 | — | 10 | 9.5 | 10 | 1 | 97 | 95 |
| | 21 | 10/5/ST30 | 0 | 1 | — | 8 | 10 | 9.5 | 3 | 98 | 98 |
| | 22 | 10/10/SP30 | 0 | 0 | — | 3 | 8 | 9 | 0 | 97 | 99 |
| III | 23 | 10/25***TP50 | 4 | 2 | 1 | 9 | 7 | 10 | 6 | 97 | 96 |
| | 24 | 10/50/SX30 | 0 | 1 | — | 10 | 9.8 | 10 | 3 | 100 | 98 |
| | 25 | 10/50/SP30 | 0 | 0 | — | 10 | 9 | 9.8 | 2 | 95 | 97 |
| | 26 | 15/0/SX30 | 0 | 0 | — | 10 | 10 | 9.5 | 8 | 92 | 99 |
| | 27 | EC | 5 | 2 | 3 | 9.9 | 7 | 10 | 7 | 69 | 59 |
| | 28 | EC | 0 | 2 | — | 10 | 10 | 9.8 | 5 | 52 | 22 |
| IV | 29 | EC | — | 4 | 2 | 9.5 | 9 | 10 | 4 | 38 | 27 |
| | 30 | EC (immediate incorporation) | — | — | — | — | — | — | — | 100 | 100 |

TABLE 1-continued

| Group | Sample | Wall Formulation | Plant Injury Rating* | | | | | | | Delayed Incorporation Percent Inhibition | |
|---|---|---|---|---|---|---|---|---|---|---|---|
| | | | Cotton | Corn | Soybean | Foxtail Millet | Pigweed | Crabgrass | Velvet Leaf | Grain Sorghum | Oats |
| | | CONTROL | 0 | 0 | 0 | 0 | 0 | 0 | 0 | 0 | 0 |

*Plant Injury Rating 0-10; 0 = no injury, 10 = plant death
**HMDA = hexamethylene diamine replaces usual amines in formulation.
*** = terephthaloyl chloride replaces sebacoyl chloride (sample 23)

Table 1 is divided into four numbered groups. Group 1 covers those samples (1-6) of microencapsulated trifluralin which demonstrate good to excellent herbicidal activity on the surface of the soil but less than the inhibition required, (90%) after delayed incorporation, for a commercially suitable product. Replicate samples 1 and 2 provide a lower percent inhibition on delayed incorporation than the E.C. formulation (samples 27-28). This is believed to be the result of a light weight wall having no crosslinking, the wall structure failing to sufficiently reduce the rate of escape of active herbicide from the microcapsule.

Group II includes those samples (7-19) which provide improvement in the delayed incorporation test (generally 80% inhibition) over the E.C. formulation but demonstrate less plant injury than the E.C. formulation on the surface of the soil. Sample 19 is a formulation in which only 10% solvent is used with trifluralin in the recipe for preparing the microencapsulated product. When the solvent is less than 20%, the trifluralin migrates from the capsule and crystalizes in the aqueous phase during storage.

Group III are those samples (20-26) which proved to be (i) superior to the E.C. formulation on delayed incorporation and (ii) as good or better than the E.C. formulation on the surface of the soil. Furthermore, these samples demonstrate a percent inhibition in the delayed incorporation test of over 90% thereby meeting the requirement of a commercial product. Sample 22, which provides about the same plant injury rating as the E.C. formulation for pigweed and crabgrass, is the least beneficial of this group but is included because it does not injure cotton and corn in the soil surface test and provides excellent percent inhibition of plant growth on delayed incorporation.

Group IV includes the samples (27-30) of the E.C. formulation. Samples 27-29 are replicates for the same E.C. formulation used in the same test procedures. Sample 30 is that E.C. formulation which was immediately incorporated into the soil after spray application. Therefore, only delayed incorporation test observations are made for this sample. The E.C. formulation which was incorporated immediately (Sample 30) provided 100 percent growth inhibition of both grain sorghum and cultivated oats whereas when incorporation of the E.C. formulation was delayed for seven days (Samples 27, 28 and 29), the percent inhibition for both grain sorghum and for oats was considerably lower indicating a loss of strength or concentration.

Replicates of one formulation are found in all three groups, i.e., samples 3, 7 and 20 (all 5/10/ST50) are respectively in Groups I, II and III. The reason for the difference in performance is not known, nevertheless, the results, except for the plant injury data for sample 7, are reasonably close. Other samples in Table 1, which display difference performance resulting in their being placed in different groups, each have some variation in the microencapsulation formulation which may account for some differences. For example, the solvent is replaced with a different solvent in samples 6 and 13 or 14; in some samples there is a variation in the amount of crosslinking agent used to replace the difunctional acid-derived reactant; in other samples there is change in the wall weight of the microcapsule; and in still other samples there is a difference in the amount of solvent used with the trifluralin. It is noted that the capsule walls of the samples of preferred Group III, except for sample 26, are all crosslinked. The wall of sample 26 (a polyamide), although not crosslinked, is heavier (15%) than the walls of the other samples (5-10%) of this group and thereby also affords the optimum control of the release rate of trifluralin. In general, it may be said that when the wall weight is 10% or less there must be at least some crosslinking of the capsule wall in order to provide a wall structure capable of sufficiently inhibiting the release of the trifluralin from the capsule. On the other hand, to permit the release of trifluralin for effective herbicidal activity of the microcapsules on the soil surface, the crosslinking (as defined hereinafter) should be less than 100% when the wall weight is 10% or greater.

The effect on volatility of different solvents for trifluralin dissolved in said solvents and encapsulated with two different capsule walls prepared by the interfacial polycondensation procedure described hereinafter is also investigated in a test procedure. The solvents used are xylene and Panasol AN-2, an aromatic petroleum (naphtha) solvent. The data for these tests are developed in a procedure wherein samples of microencapsulated trifluralin (70 parts of trifluralin dissolved in 30 parts by weight of solvent) and an E.C. formulation, each sample containing a known amount of trifluralin, are placed on filter paper in an oven heated to 54° C. and having a conventional forced air draft. At the end of a specified time period, the filter paper is analyzed to determine the loss of trifluralin. The results of the volatility tests are set forth in the following table. The dash lines under the volatility section of the table indicate that no analysis was made for the sample at that time.

TABLE 2

| Sample No. | Wall Formulation | Solvent | Volatility, %* Hours | | | |
|---|---|---|---|---|---|---|
| | | | 1 | 2 | 19 | 24 |
| 31 | 10/50/SX30 | Xylene | 19 | 22 | 30 | — |
| 32 | 10/50/SP30 | Panasol AN-2 | .4 | .7 | — | 8.5 |
| 33 | 10/5/SX30 | Xylene | 80 | — | — | — |
| 34 | 10/5/SP30 | Panasol AN-2 | 57 | 67 | 68** | — |
| 35 | E.C. | None | 90.3 | 94.5 | — | — |

*Volatility, % = analysed loss of trifluralin in percent after specified hours, based on the original weight of trifluralin.
**68% loss after 5 hours It is evident from the data in the above table that the high degree of crosslinking of the microcapsule wall which occurs in samples 1 and 2 when 50% of the sebacoyl chloride is replaced in the polycondensation recipe with the polyfunctional PAPI (polymethylene polyphenylisocyanate), reduces the amount of volatilization of trifluralin under the test conditions compared to encapsulation walls having the low degree of crosslinking that occurs, for example, when 5% of sebacoyl chloride is replaced with PAPI (Samples 3 and 4). Furthermore, an exchange of the solvent from xylene to the heavier Panasol also reduces the volatility of the encapsulated trifluralin. The E.C. formulation demonstrates a comparatively high volatility under the test conditions, as is to be expected.

Volatility and herbicidal activity of samples of microcapsules of trifluralin prepared with walls of increasing wall weight are tested. Samples are prepared using the interfacial polycondensation procedure hereinafter described to provide one sample having a wall weight of 10 percent, the next a wall weight of 20 percent, and the third a wall weight of 30 percent, based on the total weight of the microcapsule. Each of the polycondensation recipes include PAPI to replace 25% of the acid-derived difunctional reactant, adipoyl chloride. 70 parts of trifluralin dissolved in 30 parts by weight of Panasol AN-2 comprise the capsule contents. The volatility test procedure is the same as that described in connection with Table 2 above. Data for the herbicidal activity of the samples is obtained in a field test in which the herbicide is applied to the soil by spraying at a rate of 0.5 pound per acre and then raked (incorporated) into the top 1-3 inches of soil at the specified number of days. Rye gress seeds are planted immediately after the herbicide is incorporated into the soil and a count of the number of germinated rye grass plants is made two weeks after each planting. The results of these tests are given in the following table. Dash lines in the table indicate that no test results were obtained for the sample at the given time.

pared to an E.C. formulation of the identical herbicide, applied at the same rate, which is immediately incorporated into the soil after application. Furthermore, a preferred microencapsulated product of this invention also provides as good herbicidal activity on the soil surface with no greater damage to food crops as the E.C. formulation remaining on the soil surface.

While the preferred active herbicide for this invention is trifluralin (di-n-propyl derivative), herbicides wherein the alkyl groups of the toluidine compound are for example, methyl, ethyl, isopropyl, n-butyl, isoamyl, 1-methylisobutyl and the like are included. These derivatives may be used to replace trifluralin or may be used in a mixture therewith. In addition, it is contemplated that other herbicides which are compatible with the toluidene herbicide mentioned above, may be used in an admixture consisting of a major proportion of the toluidine compound in the microcapsules of this invention.

The Herbicide Solution

In addition to the use of the microcapsule wall, as defined herein, to encase the toluidine herbicide, it has been found necessary to employ a non water-soluble organic solvent to form a solution of the herbicide for encapsulation by interfacial polycondensation and when used in the specified amounts, the solvent helps to provide effective release rates of the herbicide from the microcapsule. Examples of non water-soluble solvents which may be used for this invention include typical aromatic petroleum solvents, e.g. xylene, toluene and naphtha; heptane, cycloheptane, chloroform, isobornyl acetate, isopropylbenzene, methylene chloride, propylene dichloride, soybean oil and the like.

The preferred solvents for this invention are the aro-

TABLE 3

| Sample No. | Wall Formulation | Volatility, % Hours | | | | | | Rye Grass Counts Herbicide Incorporation (days) | | | | |
|---|---|---|---|---|---|---|---|---|---|---|---|---|
| | | 1 | 2 | 3 | 4 | 16 | 20 | 0 | 1 | 2 | 3 | Total |
| 36 | 10/25/AP30 | 49 | 63 | 66 | — | — | — | 26 | 32 | 23 | 8 | 89 |
| 37 | 20/25/AP30 | — | 20.5 | — | — | 32.6 | 37.3 | 14 | 6 | 19 | 13 | 52 |
| 38 | 30/25/AP30 | 15.3 | — | 16.8 | — | — | 15.8 | 24 | 38 | 32 | 19 | 113 |
| 39 | EC | 90.3 | 94.5 | — | — | — | — | 18 | 35 | 34 | 40 | 127 |
| | Check (no Herbicide) | | | | | | | 75 | 78 | 84 | 86 | 323 |

The volatility data in Table 3 indicate that the loss of trifluralin by volatilization decreases under the test conditions as the capsule wall weight is increased. The capsule wall prevents the rapid loss of trifluralin which occurs with the E.C. formulation. In the second portion of the table, the tendency of the E.C. formulation to permit more grass germination as incorporation is delayed, is shown. Conversely, the encapsulated trifluralin samples demonstrate a level-off or decrease in germination as incorporation of the herbicide into the soil is delayed. These data also show that the activity of the encapsulated formulations and the E.C. are essentially the same when both are immediately incorporated in the soil after application, i.e. at 0 days.

Discussion-Generic

The microencapsulated organic solvent solution of alpha, alpha, alpha-trifluoro-2,6-dinitro-N,N-di ($C_1$-$C_5$) alkyl-p-toluidine discussed herein is a product which unexpectedly demonstrates decreased volatility when on the surface of the soil but substantially equivalent activity, when incorporated into the soil after a prolonged period of time on the surface of the soil, commatic petroleum solvents because they are approved as an inert ingredient for use on growing crops under federal regulations and they are known to be compatible with the toluidine herbicides defined herein.

The amount of solvent which is used in the solution with the toluidine herbicide will range from 20 to about 60%, preferably from 30 to about 50%, based on the weight of the solution. During storage, trifluralin tends to migrate from the microcapsules into the aqueous phase of the dispersion when the solvent in which it is dissolved is less than 20 weight% or even less than 30 weight% depending on the nature of the solvent. On the other hand, capsules containing greater than 50-60 weight% solvent become much less economically attractive for large scale application.

Microcapsule Preparation

In general, the microencapsulation procedure as used herein is described in U.S. Pat. Nos. 3,429,827 and 3,577,515 and involves interfacial condensation of complementary, organic, polycondensate-forming intermediates reacting to form an amide-urea copolymer, a polyurea or a polyamide resinous capsule wall about the herbicide solution. The procedure comprises (1) establishing by agitation, a dispersion of to-be-encapsulated droplets containing a first of said intermediates in a body of liquid which is (i) in continuous phase, (ii) immiscible with the droplets and (iii) essentially free of any reactant complementary to said first intermediate, and (2) thereafter bringing a second of said intermediates, i.e., complementary to the first intermediate, into the continuous liquid phase so that the first and second intermediates react at interfaces between the droplets and the continuous phase to encapsulate the droplets within a wall of said polycondensate.

To obtain crosslinking of the wall-forming condensate polymer chains during the polycondensation reaction, at least one of said first and second intermediates comprises at least in part a polyfunctional reactant which (a) is complementary to the other of said intermediates and effective for crosslinking reaction and (b) has at least three reactive groups that are the same as each other and are selected from the class consisting of amine, isocyanate, —COCl and $SO_2Cl$ groups, said first and second intermediates thereby reacting to encapsulate the droplets within the aforesaid polycondensate wall having crosslinking therein.

While the percent of crosslinking, as reported herein, is that theoretically obtained when an amount of polyfunctional reactant is used to replace a given amount of difunctional reactant (percent crosslinking is based on 100% yield in the polycondensation reaction) in reality, the polycondensation reaction does not go to completion (a 100% yield on polycondensation is not obtained but a yield in excess of 90% is generally expected). Consequently, actual crosslinking is somewhat less than that theoretically possible or as credited herein to the various encapsulation wall formulations.

While both of said first and second intermediates can consist entirely of polyfunctional reactants, as described above, whereby each reactant is able to crosslink with a complimentary crosslinking group on an adjacent polymer chain to obtain what may be termed a polycondensate wall which can be 200% crosslinked, it is preferred that only one of said first and second intermediates contain up to 100 percent of said polyfunctional reactant. (100% crosslinked). In a more preferred embodiment of this invention, the capsule wall polymer is prepared with a polyfunctional crosslinking reactant replacing from 5 to 50% of a difunctional reactant (5-50% crosslinked).

An exemplary recipe for forming the polycondensate capsule wall about the organic solvent solution of trifluralin is as follows: Polyfunctional isocyanate, e.g., polymethylene polyphenylisocyanate (PAPI), x moles, where x equals 0 to 1; Diacid chloride, e.g., sebacoyl dichloride or difunctional isocyanate, e.g., toluene diisocyanate, 1−x moles; Difunctional amine, e.g., ethylene diamine, n−y moles, where n equals 1 to 3; difunctional polyamine, e.g., diethylene triamine, y moles, where y=0 to 1.5; in addition, a base such as sodium hydroxide may be included in the recipe to neutralize hydrochloric acid generated during the polycondensation reaction. Excess amine may be present in the recipe. The diacid chloride and/or isocyanate are added to the trifluralin solution which acts as a water-insoluble organic solvent, this organic mixture is dispersed in water and the amine is charged to the reaction as an aqueous solution.

Examples of suitable diamine and polyamine reactants to form the amide-urea copolymer, polyurea or polyamide capsule wall are ethylene diamine, phenylene diamine, toluene diamine, hexamethylene diamine, diethylene triamine, piperazine, 1,3,5-benzenetriamine trihydrochloride, 2,4,6-triaminotoluene trihydrochloride, tetraethylene pentamine, pentaethylene hexamine, polyethyleneamine, 1,3,6-triaminonaphthlene, 3,4,5,8-tetraaminoanthroquinone. Examples of difunctional and polyfunctional acid-derived compounds providing —COCl and —$SO_2Cl$ reactive groups are sebacoyl chloride, ethylene-bischloroformate, phosgene, azelaoyl chloride, adipoyl chloride, terephthaloyl chloride, dodecanedioic acid chloride, dimer acid chloride, 1,3-benzene tetra-acid chloride, 1,2,5-benezene trischloroformate. Intermediates useful in providing reactive isocyanate groups are represented by such compounds as paraphenylene diisocyanate, meta-phenylene diisocyanate, naphthalene-1,5-diisocyanate, 2,6-toluene diisocyanate, 4,4-diphenyl diisocyanate, the dichloro diphenyl methane diisocyanates, bibenzyl diisocyanate, bitolylene diisocyanate, the diphenyl ether diisocyanates, the dimethylidiphenyl diisocyanates, the polymethylene polyphenylisocyanates, triphenylmethane-4,4',4''-triisocyanate, isopropyl benzene diisocyanate and the like.

Microencapsulated Trifluralin Formulations

The microencapsulated trifluralin formulations used to obtain the data in the tables of the foregoing Example were prepared using the following procedure wherein the difunctional and polyfunctional reactants were replaced or used in varying amounts so as to produce different capsule walls of the identity, weight and degree of crosslinking as shown in the Example. The solvent was replaced, or varied in amounts, so as to obtain the given solution of herbicide within the capsule.

To prepare a sample of (15/5/SP30) microencapsulated trifluralin having (i) a wall weight of 15% based on the weight of the microcapsule (wall & capsule content); (ii) 5% crosslinking, (i.e., 5% by weight of the difunctional reactant, sebacoyl chloride, is replaced with the polyfunctional crosslinking reactant, PAPI); and (iii) the trifluralin dissolved in an organic solvent at a weight ratio of 70 parts of trifluralin to 30 parts of solvent, the following recipe is used:

10 g of trifluralin is warmed with 4.3 g of the solvent (Panasol AN-2) and stirred until the mixture is homogenous (solution concentration=70 weitht% trifluralin). 2.43 g of sebacoyl chloride and 0.14 g of PAPI (polymethylene polyphenylisocyanate at 5% based on the weight of the non-water soluble reactants) are added to the above solution to provide the complete organic mix. The organic mix is poured, over a 15 second period, into 25 g of an aqueous solution of 0.25 weight% polyvinyl alcohol (Gelvatol) in a 100 ml. tall form glass beaker while the solution is agitated with a Kraft Model S-30 stirrer apparatus having a Model 25-A non-aerating stirrer attachment operating at high speed (about 10,000 rpm). This procedure forms droplets of the organic mix dispersed in the aqueous solution. The droplet size, and ultimately the size of the microcapsule, is controlled by the mixer speed. A mixture of 0.64 g of ethylenediamine, 0.74 g of diethylenetriamine and 0.82 g of sodium hydroxide in 10 ml. of water is then added to the aqueous solution while agitation is continued at the same high speed to thereby form a slurry in which microcapsule walls begin to form about the droplets by interfacial polymerization. After about 30-60 seconds, the stirrer speed is reduced to about 1000 rpm and stirring is continued at this speed. After two hours of low speed stirring, the resulting suspension is neutralized with concentrated hydrochloric acid to a ph of 7.0 and passed through a 50 mesh screen (U.S. Series Designation, Standard Seive Opening of 300 microns) to remove over-size capsules. The screened suspension contains at least a major proportion of microcapsules which are in excess of 10 microns and less than 100 microns in diameter. Some of the water is removed from the suspension by decantation and the resulting mixture is thickened with a sufficient amount of a xanthan gum to prevent settling (about 0.3% based on weight of mixture).

Production equipment for preparing the microencapsulated herbicide generally consists of three separate vessels and a mixing apparatus with which up to 2000 gallons of an aqueous suspension of microencapsulated product is produced. In the first vessel, the organic mix, consisting of appropriate amounts of active ingredient (e.g., sebacoyl chloride) and polyfunctional reactant (e.g., PAPI), if used, is prepared by mixing with a conventional mechanical stirrer. The second vessel contains water and an emulsifier (e.g., polyvinyl alcohol) which serves as a continuous phase on mixing. The third vessel is the reactor comprising a glass or plastic tank (2000 gal. capacity) equipped with stirring and cooling means. Difunctional reactant (e.g., amine), complementary to the acidic reactant caustic and water in appropriate amounts are the initial components in this vessel. When starting the flow of reactants in the process, the organic mix in the first vessel and aqueous solution of emulsifier in the second vessel are run together through a two inch, in-line mixer consisting of an encased in-line impeller and stator (Greerco Co.-Massachussetts), at an impeller speed of 5000–10,000 rpm. The impeller speed determines the size of the capsules. The emulsion formed in the in-line mixer is dropped into the aqueous solution of complimentary difunctional reactant in the reactor (third vessel) under agitation. Agitation of the reactor contents is continued for up to two hours (for a 2000 gal. batch) and then the dispersion in the reactor is neutralized with HCl to about pH7. The neutralized dispersion is pumped from the reactor through a screen (about 50 mesh-ASTM E11) to remove over-size particles, and into a gel tank where a thickening or suspending agent is stirred in for several hours. The dispersion is then ready for packaging.

Microcapsule Suspensions

A suspension or slurry of the microcapsules in water at a concentration of active ingredient of from about 15–30% preferably 20–25%, based on the weight of the suspension, is the usual embodiment for storage and shipping. This suspension of microencapsulated herbicide may have incorporated therein suspending agents, for example, crosslinked acrylic acid interpolymers are disclosed in U.S. Pat. No. 3,426,004; xanthan gum as disclosed in U.S. Pat. No. 4,107,191; hydroxyethyl cellulose, gums, clays submicron-size silica, and other inorganic materials; and wetting agents and dispersants including polyvinyl alcohol, gelatin, methyl cellulose, casein, clays and various detergents.

To provide an aqueous dispersion or suspension of microencapsules capable of spray application, the thick, concentrated (15–30%) dispersion mentioned above is diluted by the applicator with water to the point where it can be readily sprayed with equipment used for aerial or ground application. A less dilute preparation is the choice for aerial application since less water and more active ingredient is transported. In general, dilution of the concentrate with water is sufficient to avoid clogging of conventional spray nozzles but less than that which will deter adequate coverage in one pass by the applicator. The dispersion of microcapsules as applied, will, for example, range in concentration from about 1 to 12% active ingredient, based on the weight of the dispersion, or about 0.1 to about 1.0 pound of active ingredient per gallon. The applicator applies this diluted dispersion at the rate of from about 0.25 to about 2.0 pounds, preferably about 0.5 to 1.5 pounds of active ingredient per acre.

Microcapsule Dimensions

Particle Size

Aqueous dispersions wherein the average particle size (diameter) of the dispersed microcapsules is less than 10 microns are impractical because such dispersions tend to drift excessively on aerial application making coverage of an area at a specified application rate extremely difficult. On the otherhand, the use of aqueous dispersions containing microcapsules having an average particle size in excess of 100 microns with conventional spray equipment can result in spray nozzle clogging problems. Consequently, the average particle size of the microcapsules in the aqueous dispersion of this invention will be at least 10 microns and will not exceed about 100 microns and the particle size will range from about 5 to no greater than 250 microns in diameter. The preferred average particle size of the microcapsules is from about 25 to about 50 microns. The size of the microcapsules is controlled during the process of encapsulation by using mixing, stirring or agitating means at a suitable rate of speed to form droplets of the to be encapsulated ingredients which are of the size or slightly smaller than the desired size of the resulting microcapsules, as previously explained.

The particle size of the microcapsules of this invention are measured either by using a microscope with a calibrated reticle and visually estimating the average particle size, or the size can be determined using a Coulter Counter. Microscopic determination generally is within ±5 microns of that size measured by the Coulter Counter. The Coulter Counter determines by electronic means the particle size distribution of the particles making up a test sample. From this distribution, $d_{16}$, $d_{50}$ and $d_{84}$ values are determined. These values are selected because they produce a convenient straight line in a log probability plot. $d_{16}$ represents the size (diameter in microns) which 16 weight percent of the capsules in the sample are equal to or larger than, $d_{50}$ represents the size which 50 weight percent of the capsules are equal to or larger than, and $d_{84}$ represents the size which 84 weight percent of the capsules are equal to or larger than. The $d_{16}$, $d_{50}$ and $d_{84}$ values for samples of microcapsules of this invention having five (5) different wall formulations are set forth in the following table.

| Coulter Counter Measurements | | | |
|---|---|---|---|
| Wall Formulation | Particle Size, Microns | | |
| | $d_{16}$ | $d_{50}$ | $d_{84}$ |
| 5/20/St23 | 50 | 30 | 19 |
| 5/35/St23 | 43 | 27 | 18 |
| 5/70/St23 | 45 | 27 | 18 |
| 10/5/St23 | 44 | 25 | 15 |

-continued

| Coulter Counter Measurements | | | |
|---|---|---|---|
| Wall Formulation | Particle Size, Microns | | |
| 10/20/St23 | 54 | 28 | 17 | t = Tennaco Aromatic Petroleum Solvent

Wall Weight

The weight of the walls of the capsules of this invention as a percent of the total weight of the microcapsules, is calculated from the amount of ingredients in the recipe for preparing the encapsulated product and assumes that the reactants chemically unite to the degree of 100% of that theoretically possible. The calculated amount may be checked by removing the water from the microcapsule dispersion, drying the capsules and weighing the dried capsules. The solvent and active ingredient in the capsule are then removed by extraction and the empty capsules reweighed.

The broad range for the capsule wall weight is from about 2.5 to about 40%, based on the weight of the microcapsules. It is preferred that the wall be at least 5% and no greater than about 15% since it is more difficult to obtain the proper release rate with walls which are lighter than about 5%, but, it is most economical to use a wall of low weight as the capsule payload will be high i.e., each capsule will contain a high amount of active ingredient.

Wall Thickness

A relationship exists between the wall thickness, capsule diameter and wall weight for the microcapsules of this invention. The wall thickness is calculated using the following equation where V equals volume of the capsule as determined from the known wall weight percent and capsule diameter, and by assuming that the density of the capsule wall polymer and the capsule contents are both 1.0.

$$\text{Wall Thickness} = \sqrt[3]{\frac{3V}{4\pi}} - \sqrt[3]{\frac{100 - \% \text{ wall weight } (3V)}{100 (4\pi)}}$$

When plotting the relationship between wall thickness (as calculated from the above formula) and capsule diameter (or capsule volume) for two samples of microencapsulated trifluralin having wall weights of 10% and 20%* (based on the weight of the microcapsule), respectively, the following ranges of wall thickness are developed for capsule diameters increasing from about 6 up to 125 microns.

*—The amount of crosslinking of the capsule wall, the identity of the acid-derived reactant of the polycondensation recipe and the identity and amount of solvent (within the range of 20–60 weight %) are not considered significant in determining wall weight.

| Wall Weight (%) | Wall Thickness range (microns) |
|---|---|
| 10 | 0.1–3 |
| 20 | 0.3–7 |

I claim:

1. A herbicide product comprising an aqueous dispersion of microcapsules of a solution of alpha, alpha, alpha-trifluoro-2,6-dinitro-N,N-di($C_1$–$C_5$) alkyl-p-toluidine dissolved in at least 20% up to about 60% of an aromatic petroleum solvent, based on the weight of said solution, said toluidine being present in said dispersion in a phytotoxic amount, said solution microencapsulated within a resinous polycondensate wall selected from the group consisting of polyurea, polyamide and amide-urea copolymers, the weight of said wall ranging from 2.5 to 40% based on the weight of the microcapsule, at least a major proportion of said microcapsules having an average size of at least about 10 up to about 100 microns in diameter, said polycondensate wall prepared by the reaction of first and second polyurea, polyamide or amide-urea copolymer-forming intermediates, at least one of said first and second intermediates containing from 0 to 100 percent, based on the weight of the intermediate, of a polyfunctional reactant which (a) is complementary to the other of said intermediates and effective for crosslinking reaction and (b) has at least three reactive groups that are effectively functional in said reaction, said reactive groups selected from the class consisting of amine, isocyanate, —COCl and $SO_2Cl$ groups, said intermediate containing at least 5% of said polyfunctional reactant when the weight of the wall is 10% or less, and, said intermediate containing less than 100% of said polyfunctional reactant when the weight of said wall is 10% or greater.

2. The product of claim 1 wherein only one of said first and second intermediates consists of from 0 to 100 percent of said polyfunctional reactant.

3. The product of claim 2 wherein the encapsulating wall is an amide-urea copolymer.

4. The product of claim 3 wherein from about 5 to about 50 percent of said intermediate is said polyfunctional reactant.

5. The product of claim 1, 2 3 or 4 wherein said wall has a weight range of from about 5 to about 15 percent, based on the weight of the microcapsule.

6. The product of claim 5 wherein the ($C_1$–$C_5$) alkyl group of the toluidine compound is n-propyl.

7. The product of claim 2 wherein the encapsulating wall is an amide-urea copolymer, the wall has a weight of about 5 to about 15 percent, from about 5 to about 50 percent of said intermediate is said polyfunctional reactant, the ($C_1$–$C_5$) alkyl group of the toluidine compound is n-propyl, the solvent is an aromatic petroleum solvent, said solvent is present in an amount of from about 30 to about 50 percent, based on the weight of said solution, and the average diameter of the microcapsules ranges from about 25 to about 50 microns.

8. The product of claim 7 wherein said amide-urea copolymer is the result of the interfacial polycondensation of a difunctional amine, sebacoyl chloride and polymethylene polyphenylisocyanate, said isocyanate being said polyfunctional reactant.

9. A method of selectively destroying germinating weed seeds and seedlings comprising applying the aqueous dispersion of claim 1 to the soil to be treated at the rate of about 0.25 to about 2.0 pounds of active herbicide per acre and, within seven days of the application, incorporating the herbicide product into the top three inches of the surface of the soil.

10. The method of claim 9 wherein said application is by aerial spraying.

* * * * *